US011759129B2

(12) United States Patent
Cui et al.

(10) Patent No.: US 11,759,129 B2
(45) Date of Patent: Sep. 19, 2023

(54) NONINVASIVE GLUCOMETER AND BLOOD GLUCOSE DETECTION METHOD

(71) Applicant: TSINGHUA UNIVERSITY, Beijing (CN)

(72) Inventors: Kaiyu Cui, Beijing (CN); Xusheng Cai, Beijing (CN); Hongbo Zhu, Beijing (CN); Yidong Huang, Beijing (CN); Xue Feng, Beijing (CN); Fang Liu, Beijing (CN); Wei Zhang, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 287 days.

(21) Appl. No.: 16/978,122

(22) PCT Filed: Aug. 21, 2019

(86) PCT No.: PCT/CN2019/101773
§ 371 (c)(1),
(2) Date: Sep. 3, 2020

(87) PCT Pub. No.: WO2021/017052
PCT Pub. Date: Feb. 4, 2021

(65) Prior Publication Data
US 2022/0061672 A1    Mar. 3, 2022

(30) Foreign Application Priority Data

Jul. 31, 2019   (CN) .......................... 201910700382.1

(51) Int. Cl.
*A61B 5/1455*   (2006.01)
*A61B 5/145*   (2006.01)

(52) U.S. Cl.
CPC ........ *A61B 5/1455* (2013.01); *A61B 5/14532* (2013.01); *A61B 2562/0233* (2013.01)

(58) Field of Classification Search
CPC .............. A61B 5/1455; A61B 5/14532; A61B 2562/0233; A61B 5/7257; A61B 5/0075;
(Continued)

(56) References Cited

U.S. PATENT DOCUMENTS 5,515,847 A    5/1996  Braig et al.
6,040,936 A *  3/2000  Kim .................... G02F 1/13338
                                                    359/251
(Continued)

FOREIGN PATENT DOCUMENTS

CN    102564586    *  7/2012  ................ G01J 3/02
CN    102928394 A    2/2013
(Continued)

OTHER PUBLICATIONS

Przybilla et al., "Long vs. short-range orders in random subwavelength hole arrays", Optics Express, vol. 20, No. 4, Feb. 9, 2012 (Year: 2012).*

(Continued)

*Primary Examiner* — Eric F Winakur
*Assistant Examiner* — Jonathan Drew Moroneso

(57) ABSTRACT

A noninvasive glucometer and a blood glucose detection method are provided. The noninvasive glucometer includes a light source, a spectrometer and detecting space into which an object to be detected intervenes; the detecting space is connected with the light source and the spectrometer respectively, so that a spectrum emitted by the light source can generate incident light entering the spectrometer after passing through the object to be detected. The spectrometer includes: an optical modulation layer configured to perform light modulation on the incident light to obtain a modulated spectrum; a photoelectric detection layer located below the optical modulation layer, and configured to receive the modulated spectrum and provide differential responses with (Continued)

respect to the modulated spectrum; and a signal processing circuit layer located below the photoelectric detection layer and configured to reconstruct the differential responses to obtain an original spectrum.

18 Claims, 10 Drawing Sheets

(58) Field of Classification Search
CPC .................. A61B 5/726; A61B 5/7264; A61B 2562/0238
See application file for complete search history.

(56) References Cited

U.S. PATENT DOCUMENTS

| | | | |
|---|---|---|---|
| 2006/0063983 | A1 | 3/2006 | Yamakoshi |
| 2007/0161877 | A1 | 7/2007 | Arai et al. |
| 2012/0129269 | A1 | 5/2012 | Choi et al. |
| 2014/0061486 | A1 | 3/2014 | Bao et al. |
| 2017/0014057 | A1 | 1/2017 | Sato |
| 2017/0020431 | A1 | 1/2017 | Flitsch et al. |
| 2018/0080823 | A1* | 3/2018 | Bae .......................... G01J 3/32 |
| 2018/0228410 | A1 | 8/2018 | Yeh et al. |
| 2018/0348053 | A1 | 12/2018 | Koide |
| 2019/0261896 | A1* | 8/2019 | Poeze .................. A61B 5/7275 |

FOREIGN PATENT DOCUMENTS

| | | | | |
|---|---|---|---|---|
| CN | 202869653 | U | 4/2013 | |
| CN | 104013411 | A | 9/2014 | |
| CN | 104583760 | A | 4/2015 | |
| CN | 105193423 | A | 12/2015 | |
| CN | 205758567 | U | 12/2016 | |
| CN | 106847849 | | * 6/2017 | ............. B82Y 40/00 |
| CN | 107198530 | A | 9/2017 | |
| CN | 207457534 | U | 6/2018 | |
| DE | 69333010 | T2 | 4/2004 | |
| JP | 2003149145 | A | 5/2003 | |
| JP | 2007-259967 | A | 10/2007 | |
| JP | 2008-191097 | A | 8/2008 | |
| JP | 2015-126789 | A | 7/2015 | |
| JP | 2017-23748 | A | 2/2017 | |
| JP | 2018-205035 | A | 12/2018 | |
| JP | 2019510202 | A | 4/2019 | |
| KR | 1020050002892 | A | 1/2005 | |

OTHER PUBLICATIONS

Burgos et al., "Color Imaging via Nearest Neighbor Hole Coupling in Plasmonic Color Filters Integrated onto a Complementary Metal-Oxide Semiconductor Image Sensor", ACS NANO, 7, 10038-10047, Published Oct. 24, 2013 (Year: 2013).*
Hao et al., "CompactSuper-Wide Bandpass Substrate Integrated Waveguide (SJW) Filters", IEEE, 53, 2968-2977, Published Sep. 2005 (Year: 2005).*
Notice of Reasons for Refusal for Japanese Application No. 2020-528426 dated Dec. 21, 2021.
Notice of Reasons for Refusal for Japanese Application No. 2020-528426 dated Jul. 20, 2022.
Written Opinion of the International Search Authority for PCT Application No. PCT/CN2019/101773 dated May 9, 2020.
International Preliminary Report on Patentability Chapter I for PCT Application No. PCT/CN2019/101773 dated Feb. 10, 2022.
Written Decision on Registration for Korean Application No. 10-2020-7002587 dated Oct. 19, 2021.
International Search Report for Application No. PCT/CN2019/101773, dated May 9, 2020, 5 pages.
First Search Report for Chinese Application No. 201910700382.1 dated Apr. 6, 2023.
Extended European Search Report for European Application No. 19868158.7 dated Jul. 3, 2023.

* cited by examiner

NONINVASIVE GLUCOMETER AND BLOOD GLUCOSE DETECTION METHOD

CROSS-REFERENCE TO RELATED APPLICATION

This application is a national phase entry of International Application No. PCT/CN2019/101773, filed on Aug. 21, 2019, which is based on and claims priority to Chinese Patent Application No. 2019107003821, filed on Jul. 31, 2019, entitled "Noninvasive Glucometer and Blood Glucose Detection Method", the disclosure of all of which is incorporated herein by reference in their entirety.

FIELD OF TECHNOLOGY

The present disclosure relates to the technical field of medical detecting equipment, and particularly to a noninvasive glucometer and a blood glucose detection method.

BACKGROUND

Diabetes mellitus (referred to as DM) is a multi-cause metabolic disease caused by insufficient insulin secretion or insulin utilization disorder. It is mainly characterized by chronic hyperglycemia, accompanied by metabolic disorders of carbohydrate, fat and protein and can cause a series of serious complications. Diabetes mellitus is one of the major diseases that threaten human health. Diabetes mellitus not only greatly reduces the quality of patients' life, but also increases the global economic burden. Therefore, it is urgent to conduct relevant researches on the prevention and treatment of diabetes mellitus.

Blood glucose concentration is an important indicator reflecting the condition of diabetes mellitus. Frequently measuring blood glucose is conducive to monitoring the patient's condition and maintaining the blood glucose concentration at a normal level in time. There are three types of blood glucose detection methods: invasive, minimally invasive and noninvasive. Invasive and minimally invasive detecting methods have been put into clinical application due to their high accuracy. However, these methods often cause the patients to feel pain and discomfort due to the need for blood collection, and there is a risk of infection. In addition, since each measurement is high in the cost, the noninvasive detecting technology of blood glucose has drawn widespread attention from all communities of society.

However, the existing noninvasive glucometers have a serious problem of insufficient measurement accuracy. The measurement accuracy of a noninvasive glucometer is greatly affected by environmental and individual differences. Further, the existing noninvasive glucometers have the disadvantages of complicated operation, non-portability, disability of continuous real-time detecting and so on.

SUMMARY (I) Technical Problem to be Solved

The embodiments of the present disclosure provide a noninvasive glucometer and a blood glucose detection method, for solving the problem that the existing noninvasive glucometers have low measurement accuracy.

(II) Technical Solutions

In order to solve the technical problem above, the present disclosure provides a noninvasive glucometer, including a light source and a spectrometer, wherein a spectrum emitted by the light source can generate incident light entering the spectrometer after passing through an object to be detected;

the spectrometer includes:

an optical modulation layer configured to perform light modulation on the incident light to obtain a modulated spectrum;

a photoelectric detection layer located below the optical modulation layer, and configured to receive the modulated spectrum and provide differential responses with respect to the modulated spectrum; and a signal processing circuit layer located below the photoelectric detection layer and configured to reconstruct the differential responses to obtain an original spectrum.

In some embodiments, the optical modulation layer includes a base plate and at least one modulation unit; the base plate is provided on the photoelectric detection layer, and respective modulation units are located on the base plate; each of the modulation units is provided with several modulation holes, and respective modulation holes inside each of the modulation units are arranged into a two-dimensional graphic structure.

In some embodiments, the two-dimensional graphic structure includes that:

all the modulation holes inside respective two-dimensional graphic structures have the same specific cross-sectional shapes concurrently and the respective modulation holes are arranged in an array in an order that sizes of structural parameters are gradually varied; and/or the respective modulation holes inside the respective two-dimensional graphic structures respectively have a specific cross-sectional shape and the respective modulation holes are combined and arranged according to the specific cross-sectional shape.

In some embodiments, the arrangement order is being arranged row by row or column by column according to a preset period order when the respective modulation holes are combined and arranged according to the specific cross-sectional shape.

In some embodiments, a bottom of the modulation hole penetrates the base plate or does not penetrate the base plate.

In some embodiments, the photoelectric detection layer includes at least one detection unit, at least one detection unit is correspondingly provided below each dim light modulation unit of the optical modulation layer, and all the detection units are electrically connected through the signal processing circuit layer.

In some embodiments, the spectrometer further includes:

a light-transmitting medium layer located between the optical modulation layer and the photoelectric detection layer.

In some embodiments, the light source and the spectrometer are respectively provided on both sides of the object to be detected; or the light source and the spectrometer are provided on one side of the object to be detected.

In some embodiments, the noninvasive glucometer further includes:

a data processing module connected to the signal processing circuit layer and configured to perform analysis and calculation on the original spectrum to obtain blood glucose parameters; and a data display module connected to the data processing module and configured to display the blood glucose parameters.

The present disclosure also provides a blood glucose detection method based on the noninvasive glucometer above, including:

moving the object to be detected into the detecting space connected with the light source and the spectrometer respectively, and making the spectrum emitted by the light source pass through the object to be detected, thereby generating the incident light entering the spectrometer;

performing light modulation on the incident light to obtain the modulated spectrum;

receiving the modulated spectrum and providing differential responses with respect to the modulated spectrum; and reconstructing the differential responses to obtain the original spectrum.

(III) Advantageous Effects

The technical solutions above of the present disclosure have the following advantageous effects:

1. The noninvasive glucometer of the present disclosure includes a light source, a spectrometer and detecting space into which the object to be detected intervenes. The detecting space is connected with the light source and the spectrometer respectively, and enable the spectrum emitted by the light source generate incident light that enters the spectrometer after passing through the object to be detected. The incident light has been affected by the object to be detected because it passes through the object to be detected. Therefore, spectral analysis and reconstruction are performed on the incident light by the spectrometer to obtain the spectral data containing blood glucose parameters, so that the non-contact and non-invasive blood glucose detecting of the biological object to be detected is achieved using the principle of near-infrared spectral analysis.

2. The spectrometer in the noninvasive glucometer includes: an optical modulation layer configured to perform light modulation on the incident light to obtain a modulated spectrum; a photoelectric detection layer located below the optical modulation layer, and configured to receive the modulated spectrum and provide differential responses with respect to the modulated spectrum; and a signal processing circuit layer located below the photoelectric detection layer and configured to reconstruct the differential responses to obtain an original spectrum. The spectrometer of the noninvasive glucometer replaces various types of precise optical components in the existing spectrometers with the optical modulation layer, so as to achieve the application of the spectrometer in the field of micro-nano structures, so that the micro integrated spectrometer can operate without gratings, prisms, reflecting mirrors or other similar spatial beam splitting elements and thus the size of the spectrometer is significantly reduced meanwhile the precision of spectral analysis is improved. Therefore, the noninvasive glucometer has the advantages of high measurement accuracy, good portability, real-time online detection, simple operation, stable performance, low manufacturing costs and etc., which can greatly improve the life quality of the patients suffered from diabetes mellitus and has a broad market prospect.

BRIEF DESCRIPTION OF THE DRAWINGS

In order to more clearly describe the embodiments of the present disclosure or the technical solutions in the prior art, the drawings to be used in describing the embodiments or the prior art will be briefly described below. Obviously, the drawings in the following description are some embodiments of the present disclosure, for those of ordinary skill in the art, other drawings may also be obtained based on these drawings without any creative work.

Figure 1:
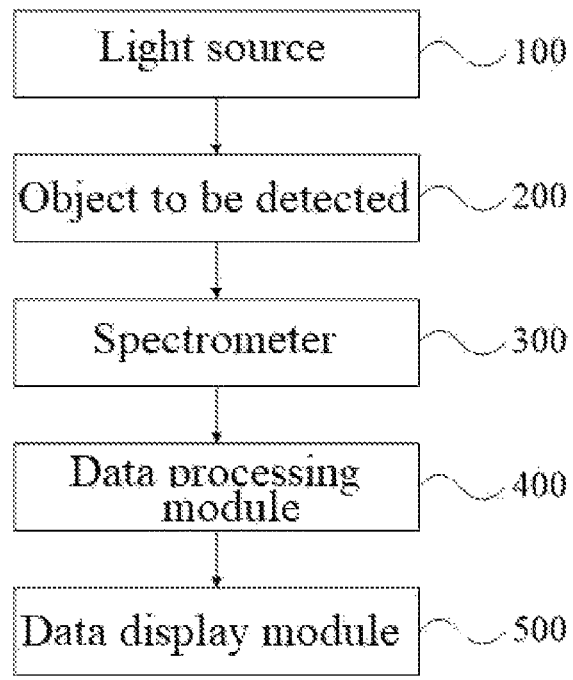
FIG. 1 is a structural diagram of the noninvasive glucometer according to an embodiment of the present disclosure.

DESCRIPTION OF THE REFERENCE NUMBERS 100 light source 200 object to be detected
300 spectrometer 400 data processing module
500 data display module 1' substrate
1 optical modulation layer 2 photoelectric detection layer
3 signal processing circuit layer 4 light-transmitting medium layer
5 modulation unit 6 modulation hole
7 detection unit 8 gap
11 first modulation unit 12 second modulation unit
13 third modulation unit 14 fourth modulation unit
15 fifth modulation unit

DETAILED DESCRIPTION

The specific implementations of the present disclosure are further described below in detail in conjunction with the accompanying drawings and embodiments. The following embodiments are used to illustrate the present disclosure, but cannot be used to limit the scope thereof. Unless specified otherwise, the glucometers mentioned in the present disclosure are all abbreviations for the noninvasive glucometer.

The detecting principles on which the existing noninvasive glucometers are based mainly include Raman spectroscopy, polarization measurement, optical coherence tomography, acousto-optic technology, bioelectrical impedance spectrum method, fluorescence detection technology, mid-infrared spectroscopy, near-infrared spectroscopy and etc. Various detecting technology principles have their own advantages and disadvantages. Among them, the near-infrared spectroscopy has become one of the most promising noninvasive blood glucose detecting technologies due to its advantages such as high accuracy, low cost, high efficiency, real-time monitoring and etc.

Based on the above-mentioned near-infrared spectroscopy, the embodiments of the present disclosure provide a noninvasive glucometer capable of achieving the non-contact and noninvasive blood glucose detecting for a biological object to be detected using the principle of near-infrared spectral analysis, and having advantages such as high measurement accuracy, good portability, real-time online detecting, simple operation, stable performance, low manufacturing costs and etc., which can greatly improve the life quality of patients suffered from diabetes mellitus, and has broad market prospects.

Specifically, as shown in FIG. 1, the noninvasive glucometer includes a light source 100 and a spectrometer 300. The light source 100 is a near-infrared light source. According to the principle of near-infrared spectral analysis, the spectrum emitted by the light source 100 can generate incident light entering the spectrometer 300 after passing through the object to be detected 200. The spectrometer 300 is capable of replacing the precise optical components in a spectrometer to achieve the precise modulation of incident light. In addition, by using the spectrometer 300, the modulation role on light having different wavelengths can be flexibly achieved. The modulation role includes, but is not limited to, the scattering, absorption, projection, reflection, interference, surface plasmon polariton, resonance of light and so on, so as to improve the differences in spectral responses between different regions, thereby improving the analytical precision of the spectrometer 300.

Specifically, as shown in FIG. 3 to FIG. 19, the spectrometer 300 includes an optical modulation layer 1, a photoelectric detection layer 2 and a signal processing circuit layer 3. A spectrum receiving surface of the optical modulation layer 1 faces the object to be detected 200, and the optical modulation layer 1 is configured to perform light modulation on the incident light to obtain a modulated spectrum. The photoelectric detection layer 2 is located below the optical modulation layer 1, and configured to receive the modulated spectrum and provide differential responses with respect to the modulated spectrum. The signal processing circuit layer 3 is connected below the photoelectric detection layer 2, and configured to reconstruct differential responses to obtain an original spectrum. The spectrometer 300 replaces various types of precise optical components in the existing spectrometers with the optical modulation layer 1, so as to achieve the application of the spectrometer 300 in the field of micro-nano structures, so that the spectrometer 300 can operate without gratings, prisms, reflecting mirrors or other similar spatial beam splitting elements, thereby significantly reducing the size of the spectrometer 300 meanwhile improving the precision of spectral analysis.

In the noninvasive glucometer of the present embodiment, the incident light affected by the object to be detected 200 carries a spectrum of the components inside the object to be detected 200, and the spectrum includes blood glucose parameters. The glucometer uses the spectrometer 300 to perform spectral analysis and reconstruction on the incident light to obtain the original spectral data inside the object to be detected 200 containing the blood glucose parameters. The information of wavelength, intensity and etc. of the obtained original spectrum can reflect the concentrations of components such as blood glucose and etc.

In addition, the noninvasive glucometer further includes a data processing module 400 and a data display module 500. The data processing module 400 is connected with the spectrometer 300, and the relevant blood glucose parameters containing the blood glucose concentration and etc. can be obtained by further calculating from the data information of the reconstructed original spectrum through the data processing module 400. The data processing module 400 includes spectral data preprocessing and a blood glucose concentration predicting model. Herein, the spectral data preprocessing refers to preprocessing the noise existing in the spectral data of the blood glucose concentration tested by the spectrometer 300. The processing methods adopted for the spectral data preprocessing include, but are not limited to, Fourier transform, differential, and wavelet transform. The blood glucose concentration predicting model includes predictions of the relevant blood glucose parameters including blood glucose concentration and the like from spectral data information. The algorithms used include, but are not limited to, least squares method, principal component analysis, and artificial neural network. The data processing module 400 is connected with the data display module 500 displaying the blood glucose parameters calculated by the data processing module 400.

Figure 2:
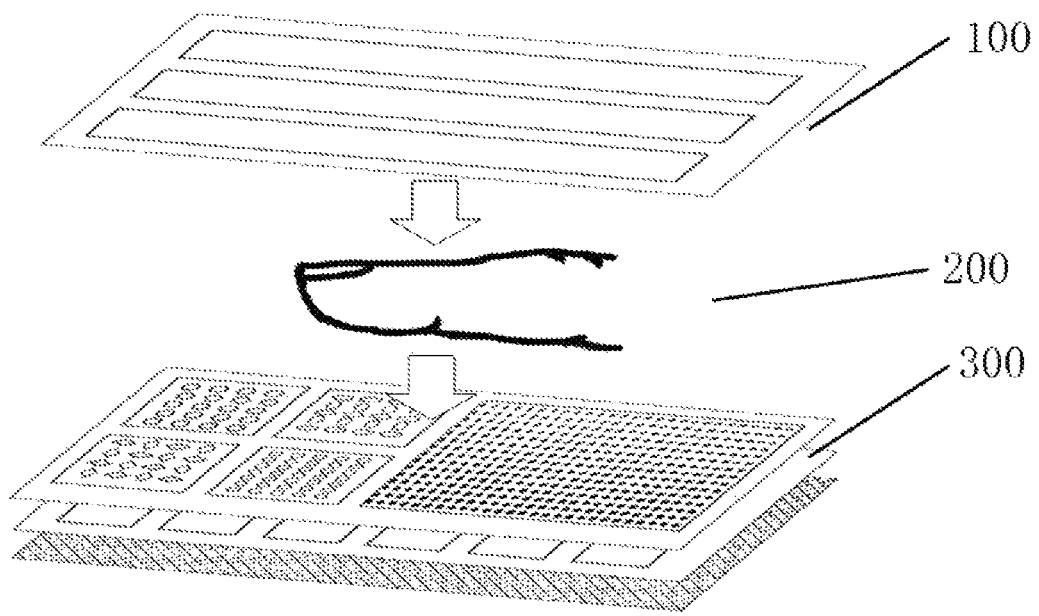
FIG. 2 is usage state diagram (I) of the noninvasive glucometer according to an embodiment of the present disclosure.

For facilitating the spectrum of the light source 100 to pass through the object to be detected 200, the light source 100 and the spectrometer 300 are preferably disposed on opposite sides of detecting space respectively, and the detecting space is disposed between the light source 100 and the spectrometer 300. Taking FIG. 2 as an example, the light source 100 and the spectrometer 300 are oppositely disposed at the upper and lower sides of the detecting space above. During detecting, the object to be detected 200 is horizontally extended into the detecting space to ensure that the near-infrared spectrum generated by the light source 100 passes through the object to be detected 200, and the incident light generated by passing through the object to be detected 200 can be directly incident into the spectrometer 300. This structural arrangement enables the near-infrared spectrum to straightly pass through the object to be detected 200, and improves the obtaining accuracy of the spectral information.

Figure 20:
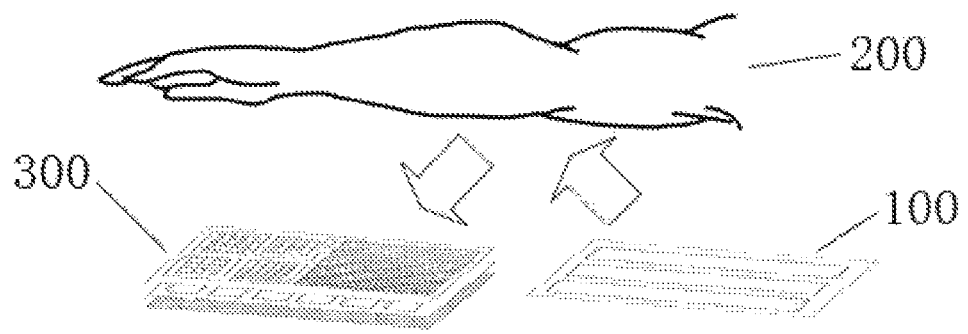
FIG. 20 is usage state diagram (II) of the noninvasive glucometer according to an embodiment of the present disclosure.

Alternatively, the light source 100 and the spectrometer 300 may be disposed on a same side of the detecting space at the same time as shown in FIG. 20, and the detecting space is on the same side with the light source 100 and the spectrometer 300. Taking FIG. 20 as an example, the light source 100 and the spectrometer 300 are simultaneously disposed on the lower side of the detecting space, and above the light source 100 and the spectrometer 300 is the detecting space. The near-infrared spectrum generated by the light source 100 can penetrate inside the object to be detected 200 for the light reflection principle, and part or all of the spectra forms the incident light entering the spectrometer 300 under the reflection effect. This structural arrangement can expand the detecting space and improve the convenience for using the glucometer.

It should be noted that, the two types of positional arrangement structures above of the spectrometer 300 and the light source 100 are applicable to the spectrometers 300 described in the various embodiments of the present disclosure.

In addition, modulation holes 6 in a same modulation unit 5 on the optical modulation layer 1 are arranged into a two-dimensional graphic structure with a specific pattern. The modulation role on light having different wavelengths is achieved by using different two-dimensional graphic structures, and the differences in spectral responses between different regions can also be improved by using the differences between the two-dimensional graphic structures, thereby improving the analytical precision of the spectrometer 300.

The spectrometer 300 in the present disclosure are described in detail below through several embodiments.

Embodiment I

Figure 3:
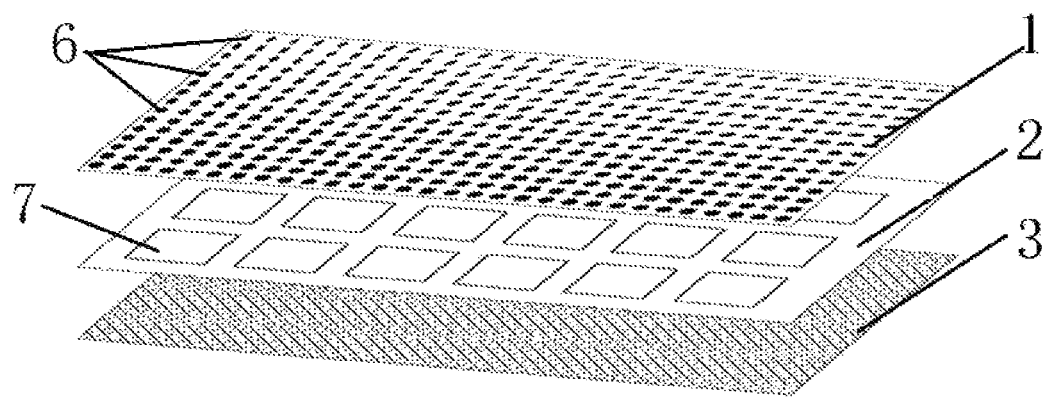
FIG. 3 is a structural diagram of the spectrometer according to Embodiment I of the present disclosure.
Figure 4:
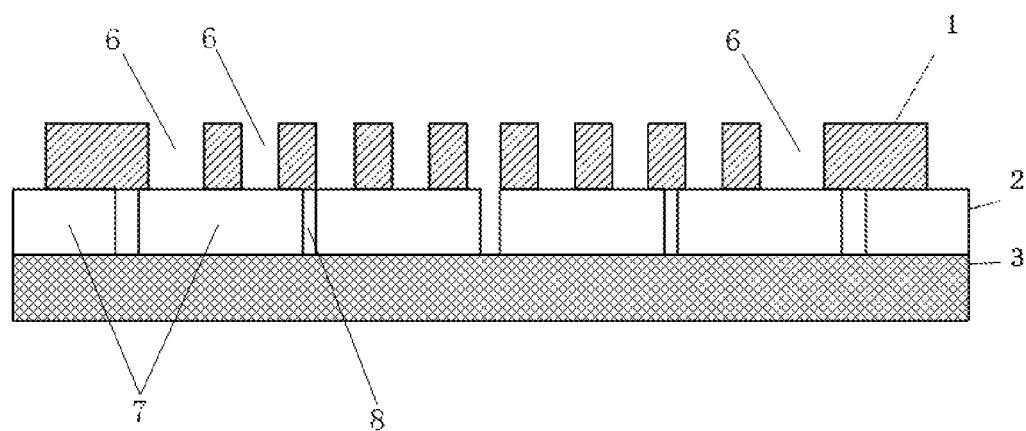
FIG. 4 is a sectional view of the spectrometer according to Embodiment I of the present disclosure.

As shown in FIG. 3 and FIG. 4, in the spectrometer 300 provided by Embodiment I, the optical modulation layer 1 includes one modulation unit 5. All the modulation holes 6 in the modulation unit 5 penetrate through a base plate. All the modulation holes 6 in the modulation unit 5 have a same specific cross-sectional shape. The oval shape shown in FIG. 1 is taken as an example in Embodiment I. All the modulation holes 6 are arranged in an array in an order that sizes of structural parameters are gradually varied to form a two-dimensional graphic structure. In this two-dimensional graphic structure, all the modulation holes 6 are arranged in an array, and all the modulation holes 6 are arranged row by row and column by column according to a length of a major axis, a length of a minor axis and an angle of rotation, from small to large, so that all the modulation holes 6 as a whole form a modulation unit 5 on the base plate of the optical modulation layer 1.

Figure 5:
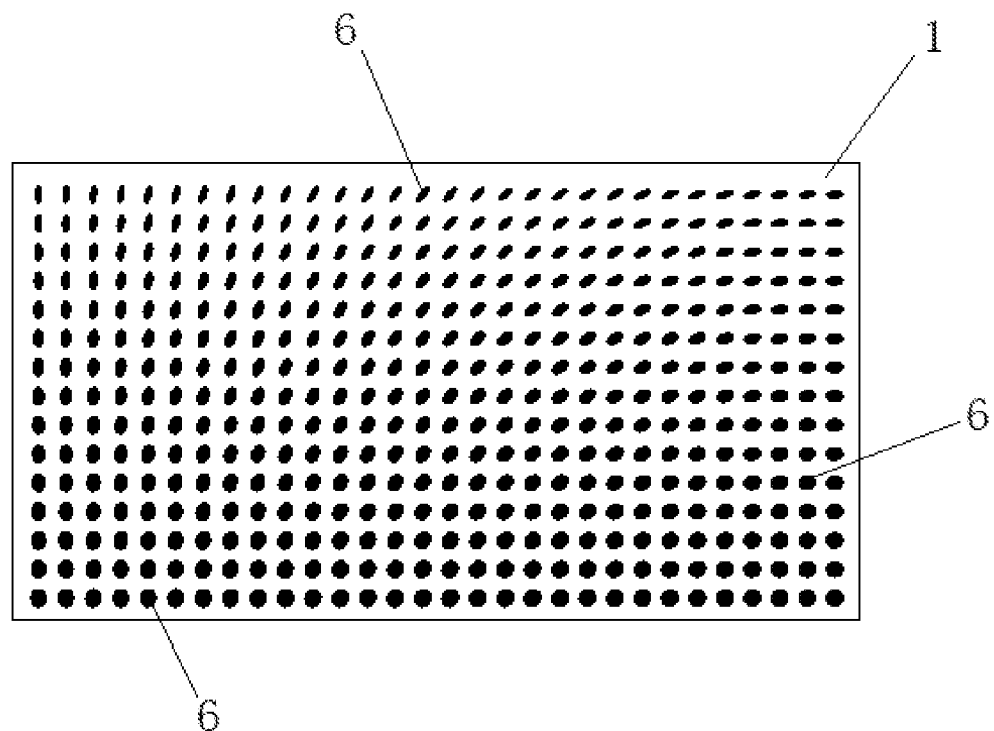
FIG. 5 is a structural diagram of the optical modulation layer according to Embodiment I of the present disclosure.

It can be understood that, as shown in FIG. 5, since all the modulation holes 6 in this embodiment are arranged according to the same pattern, that is, being gradually arranged from small to large according to the structural parameters of the length of the major axis, the length of the minor axis and the angle of rotation, row by row and column by column, all the modulation holes 6 on the optical modulation layer 1 can be regarded as an integral modulation unit 5, and can also be arbitrarily divided into several modulation units 5. The arbitrarily divided modulation units 5 have different modulating roles on the spectrum. In theory, an infinite number of modulated spectrum samples can be obtained, which dramatically increases the amount of data for reconstructing the original spectrum, and is helpful for restoring the spectral pattern of the broadband spectrum. Then, the effectiveness of the modulating roles of the modulation unit 5 on the light having different wavelengths can be determined according to the structural parameter characteristics of the modulation holes 6 inside each modulation unit 5.

It can be understood that the specific cross-sectional shape of the modulation holes 6 above includes circle, ellipse, cross, regular polygon, star, rectangle, etc., or any combination thereof. Correspondingly, the structural parameters of the modulation holes 6 above include inner diameter, length of major axis, length of minor axis, rotation angle, number of angles, or side length.

The base plate of the optical modulation layer 1 according to Embodiment I has a thickness of 60 nm to 1200 nm. The optical modulation layer 1 and the photoelectric detection layer 2 are directly connected or connected through a light-transmitting medium layer 4. The photoelectric detection layer 2 and the signal processing circuit layer 3 are electrically connected. In some embodiments, as shown in FIG. 3, all the modulation holes 6 on the optical modulation layer 1 are elliptical, and the lengths of the major axes and the lengths of minor axes of all the elliptical modulation holes 6 are increased row by row and column by column, respectively. In FIG. 3, the horizontal direction is taken as the horizontal axis, and the vertical direction is taken as the vertical axis, all the elliptical modulation holes 6 are rotated from the vertical axis to the horizontal axis row by row and column by column, and the rotation angles are gradually increased. All the modulation holes 6 constitute an overall two-dimensional graphic structure which is a matrix structure as a whole, and the area of the matrix structure ranges from 5 $\mu m^2$ to 4 $cm^2$.

When the spectrometer 300 described in this embodiment is manufactured, a silicon-based material is selected as the material of both the optical modulation layer 1 and the photoelectric detection layer 2, so as to have a good compatibility in the process of the preparation technology. When the optical modulation layer 1 is prepared, the optical modulation layer 1 may be directly generated on the photoelectric detection layer 2, or the prepared optical modulation layer 1 may be transferred to the photoelectric detection layer 2 firstly.

The direct generation of the optical modulation layer 1 specifically includes: directly growing the optical modulation layer 1 arranged according to the structure shown in FIG. 3 on the photoelectric detection layer 2 by a deposition; or installing a substrate made of the silicon-based material on the photoelectric detection layer 2, then performing micro-nano processing and perforating on the substrate according to the structure shown in FIG. 3 to obtain the optical modulation layer 1.

The process of the directly growing by the deposition above is: Step one, a silicon flat panel with a thickness of 100 nm to 400 nm (nanometer) is deposited on the photoelectric detection layer 2 through sputtering, chemical vapor deposition and etc. Step two, the desired two-dimensional graphic structure as shown in FIG. 5 is drawn on the silicon flat panel by using a pattern transfer method such as photoetching, electron beam exposure and etc. The two-dimensional graphic structure is specifically that, only the minor axes and the rotation angles of the elliptical modulation holes 6 are gradually adjusted. The major axis of the ellipse is selected from a fixed value in the range of 200 nm to 1000 nm, for example, 500 nm; and the length of the minor axis varies within the range of 120 nm to 500 nm. The rotation angle of the ellipse varies within the range of 0° to 90°, and the arrangement period of the ellipse is a fixed value in the range of 200 nm to 1000 nm, for example, 500 nm. An overall pattern range of the two-dimensional graphic structure is approximately a rectangular array structure with a length of 115 $\mu m$ and a width of 110 $\mu m$. Step three, the silicon flat panel is etched through reactive ion etching, inductively coupled plasma etching, ion beam etching and etc. to obtain the desired optical modulation layer 1. Finally, the optical modulation layer 1 and the photoelectric detection layer 2 are electrically connected as a whole to the signal processing circuit layer 3.

The transfer preparation method of the optical modulation layer 1 above is specifically: firstly, performing micro-nano processing and perforating on the substrate according to the structure shown in FIG. 3 to obtain the prepared optical modulation layer 1, then transferring the prepared optical modulation layer 1 onto the photoelectric detection layer 2. Specifically, the process of transferring the optical modulation layer 1 is that, firstly preparing the optical modulation layer 1 on a silicon wafer or SOI (referring to the silicon-on-insulator silicon wafer structure) according to the parameters above, then transferring the optical modulation layer 1 onto the photoelectric detection layer 2 with transfer methods, and finally, electrically connecting the optical modulation layer 1 and the photoelectric detection layer 2 as a whole to the signal processing circuit layer 3.

Figure 18:
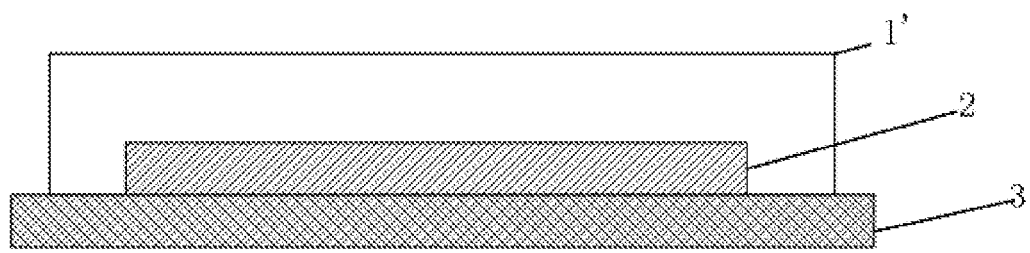
FIG. 18 and FIG. 19 are process diagrams illustrating the preparation methods for preparing and processing the modulation holes of the spectrometer according to Embodiment I to Embodiment VII of the present disclosure, respectively.
Figure 19:
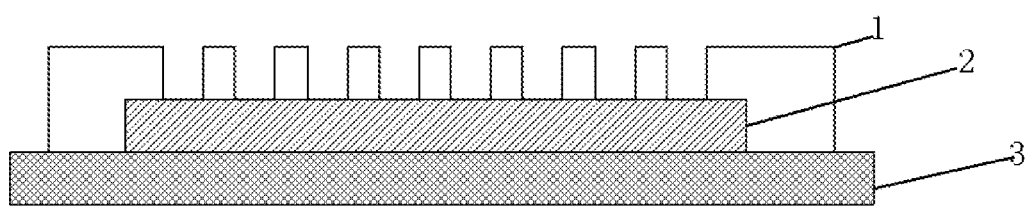

As shown in FIG. 18 and FIG. 19, this embodiment also provides another process for preparing the spectrometer 300, which is specifically that the photoelectric detection layer 2 is equipped with a III-V group detector that is specifically a GaAs/InGaAs quantum well detector. As shown in FIG. 18, the detector is reversely bonded to a CMOS circuit. The detector includes a GaAs substrate 1' and an InGaAs quantum well photoelectric detection layer 2. As shown in FIG. 19, after the substrate 1' is directly thinned, micro-nano processing is performed on the substrate 1' so as to have a two-dimensional graphic structure to form the optical modulation layer 1. The difference between this preparation process and the above-mentioned micro-nano processing and perforating only lies in that an upper surface of the photoelectric detection layer 2 composed of detectors is directly used as the substrate 1' for the micro-nano processing, thereby ensuring a tight connection between the processed and prepared optical modulation layer 1 and the photoelectric detection layer 2, and avoiding the appearance of gaps which affects the modulation effect of the light.

It should be understood that, the spectrometer 300 capable of modulating light of this embodiment includes, but is not limited to, one-dimensional and two-dimensional photonic crystals, surface plasmon polaritons, metamaterials and metasurfaces. The specific materials may include silicon, germanium, silicon germanium materials, silicon compounds, germanium compounds, metals, III-V group materials and etc. As an embodiment, the silicon compounds include, but are not limited to, silicon nitride, silicon dioxide, silicon carbide and etc. The material of the light-transmitting medium layer 4 may include materials having a low refractive index such as silicon dioxide, high-molecular polymer and etc. The photoelectric detector may be selected from a silicon detector (the detection range is 780 nm to 1100 nm), a III-V group semiconductor (such as InGaAs/InAlAs, GaAs/AlGaAs) detector (the detection range is 1000 nm to 2600 nm), an antimonide (such as InSb) detector (the detection range is 1 μm to 6.5 μm), and an HgCdTe detector (the detection range is 0.7 to 25 μm) and etc.

Figure 6:
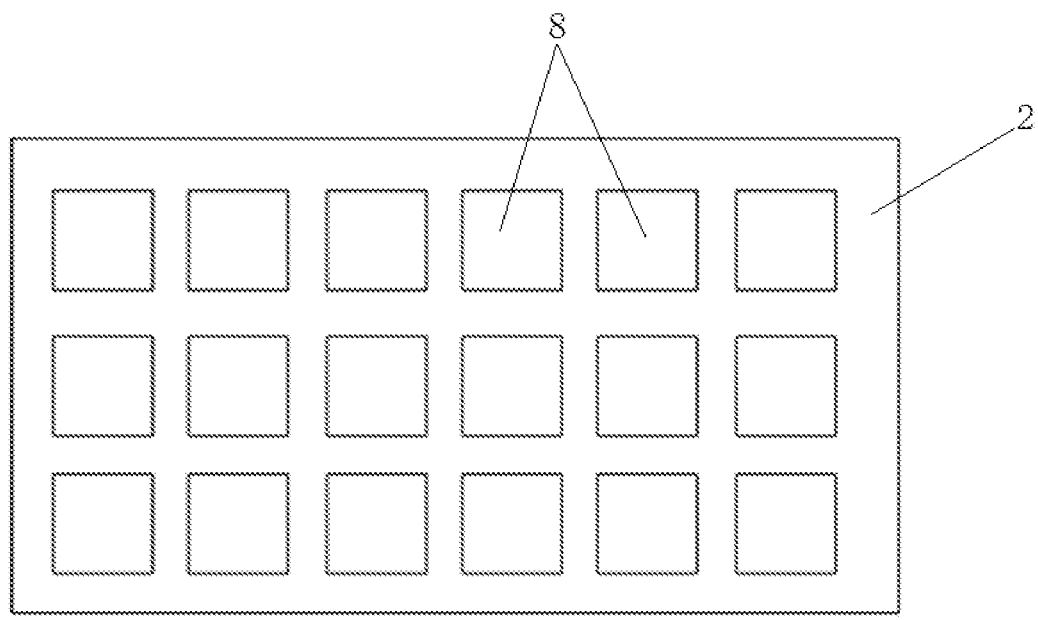
FIG. 6 is a structural diagram of the photoelectric detection layer according to Embodiment I of the present disclosure.

As shown in FIG. 4 and FIG. 6, in the spectrometer 300 described in this embodiment, the photoelectric detection layer 2 includes several detection units 7. Each detection unit 7 inside the photoelectric detection layer 2 is equipped with at least one photoelectric detector whose detection range is slightly larger than a structural range of the modulation hole 6. The photoelectric detection layer 2 in an array structure composed of several detection units 7 can transmit detected signals to the signal processing circuit layer 3 through electrical contact. The signal processing circuit layer 3 of this embodiment is equipped with an algorithm processing system capable of processing the differential responses based on an algorithm of the algorithm processing system to reconstruct the original spectrum. The differential responses refer to working out difference values between signals of the responsive spectra obtained through the modulation of each modulation unit 5. The reconstruction process is accomplished through the data processing module 400 above.

In this embodiment, several modulation holes 6 may correspond to one detection unit 7 at the same time, or each of the modulation holes 6 may correspond to one or more modulation units 7, respectively. That is to say, each modulation unit 5 corresponds in the vertical direction to one or more detection units 7. In this way, it only needs to satisfy that at least one modulation hole 6 inside the same modulation unit 5 corresponds to at least one detection unit 7. This structural arrangement ensures that the modulation unit 5 can always modulate incident light having at least one wavelength, and that the modulated light can be received by the detection unit 7. In order to prevent the detection units 7 from interfering with each other during operation, a gap 8 is preferably left between two adjacent detection units 7.

The complete process of the spectrometer 300 of this embodiment for detecting the spectrum is: firstly, modulating a spectrum with the optical modulation layer 1 when the spectrum is incident from above the optical modulation layer 1 into the spectrometer 300, to obtain different responsive spectra inside different modulation units 5. Each of the modulated responsive spectra is respectively irradiated onto the photoelectric detection layer 2, and the responsive spectra received by the detection units 7 correspondingly arranged are different from each other so as to obtain the differential responses. Finally, the signal processing circuit layer 3 uses the algorithm processing system to process the differential response, thereby obtaining the original spectrum by reconstruction.

Figure 7:
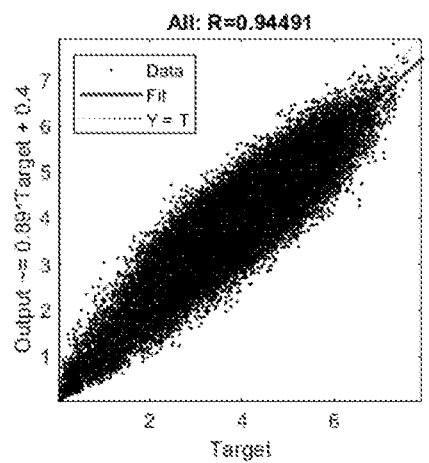
FIG. 7 is an effect diagram of the spectral detection according to Embodiment I of the present disclosure.

FIG. 7 illustrates a spectral analysis effect during spectral analysis with the spectrometer 300 obtained through actual preparation according to the embodiment above. As shown in FIG. 7, it can be known that the spectrometer 300 can detect a spectrum with a spectral range from 550 nm to 750 nm and a spectral width of 200 nm, and achieve an effect that the accuracy of measuring the spectra is greater than 94.5%.

Embodiment II

Figure 8:
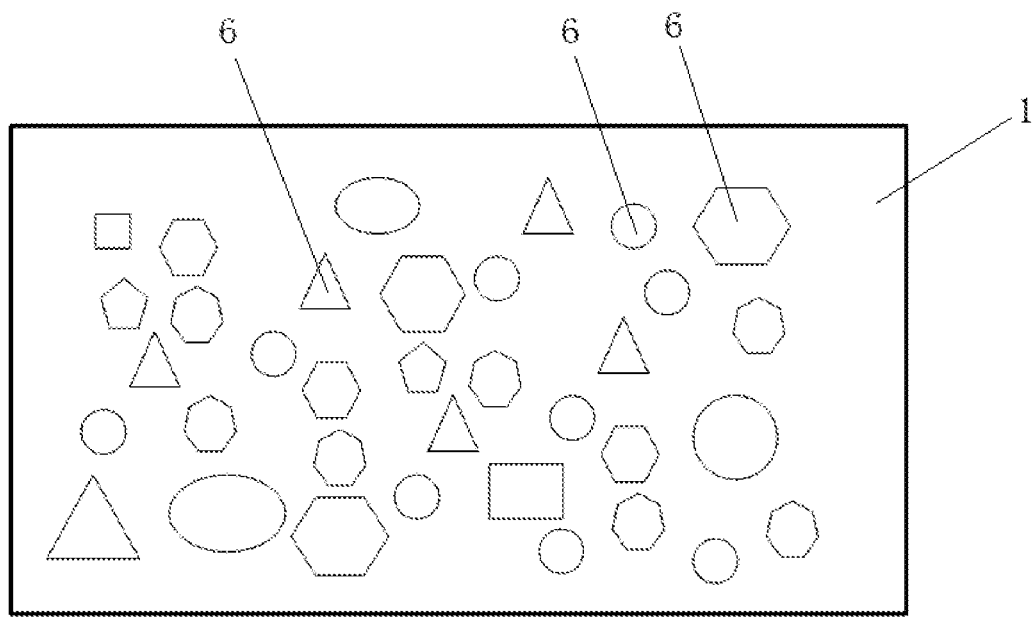
FIG. 8 is a structural diagram of the optical modulation layer according to Embodiment II of the present disclosure.

The structures, principles, spectrum modulating methods and preparation methods of the spectrometer 300 of Embodiment II are basically the same as those in Embodiment I, and the same contents are not described repeatedly, while the differences are as follows:

as shown in FIG. 8, in the spectrometer 300 of this embodiment, an integral modulation unit 5 is provided on the optical modulation layer 1. Each of the modulation holes 6 in the two-dimensional graphic structure provided in the modulation unit 5 respectively has a specific cross-sectional shape, and the respective modulation holes 6 are freely combined and arranged according to the specific cross-sectional shapes. Specifically, in the two-dimensional graphic structure, some of the modulation holes 6 have the same specific cross-sectional shapes, and the respective modulation holes 6 having the same specific cross-sectional shapes constitute a plurality of modulation hole 6 groups, and each of the modulation hole 6 groups has specific cross-sectional shapes different from each other, and all the modulation holes 6 are freely combined.

It can be understood that, the modulation unit 5 as a whole can be regarded as modulating a spectrum having a specific wavelength, or can be freely divided into several modulation units having modulation holes 6, so as to be able to modulate the spectrum having multiple different wavelengths, thereby increasing the flexibility and diversity of light modulation.

Embodiment III

Figure 9:
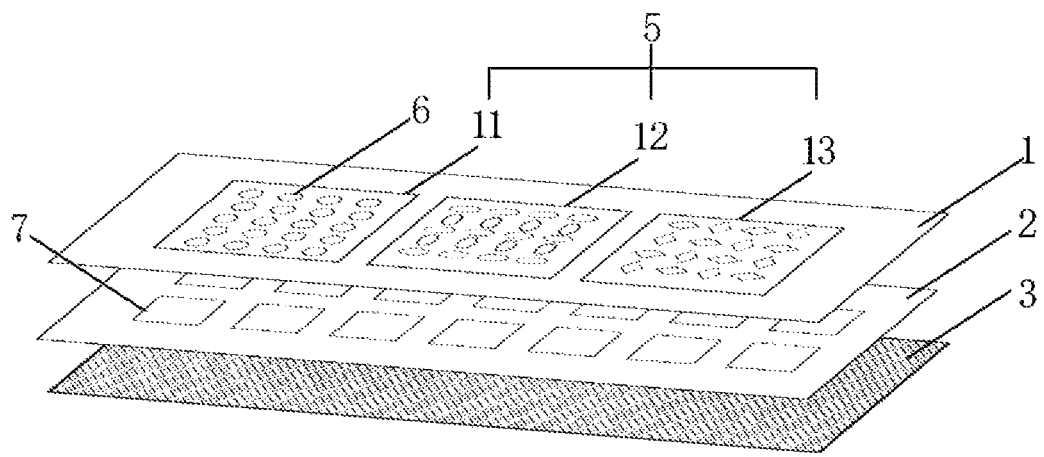
FIG. 9 is a structural diagram of the spectrometer according to Embodiment III of the present disclosure.
Figure 10:
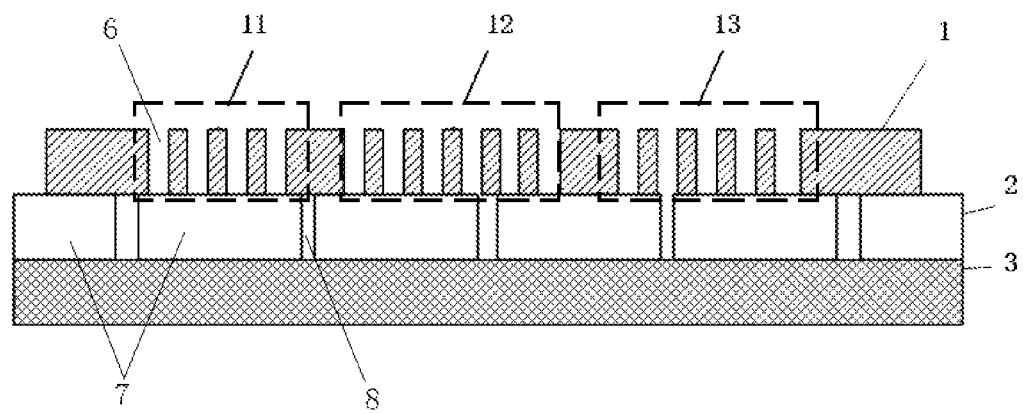
FIG. 10 is a sectional view of the spectrometer according to Embodiment III of the present disclosure.

The structures, principles, spectrum modulating methods and preparation methods of the spectrometer 300 of Embodiment III are basically the same as those in Embodiment II, and the same contents are not described repeatedly, while the differences are as follows:

as shown in FIG. 9 and FIG. 10, two or more modulation units 5 are arranged on the modulation unit 1 of the spectrometer 300 in this embodiment. In each modulation units 5, when respective modulation holes 6 are arranged and combined according to a specific cross-sectional shape, the arrangement order is being arranged row by row or column by column according to a preset period order.

In this embodiment, all the modulation holes 6 are divided into several modulation units 5 according to the specific cross-sectional shapes, and the modulation holes 6 inside the respective modulation units 5 have specific cross-sectional shapes different from each other. The modulation holes 6 inside the same modulation unit 5 have a same specific cross-sectional shape, but each of the modulation holes 6 is arranged in an array in an order that the sizes of the structural parameters are gradually varied. As a result, each modulation unit 5 has different modulation roles, and can modulate the spectrum having different wavelengths. By changing the gradual order of the structural parameters of the modulation holes 6 inside the modulation units 5 and/or the specific cross-sectional shapes of the modulation holes 6 according to the modulation requirement, the modulation role and/or the modulated object of the current modulation unit 5 can be changed.

Figure 11:
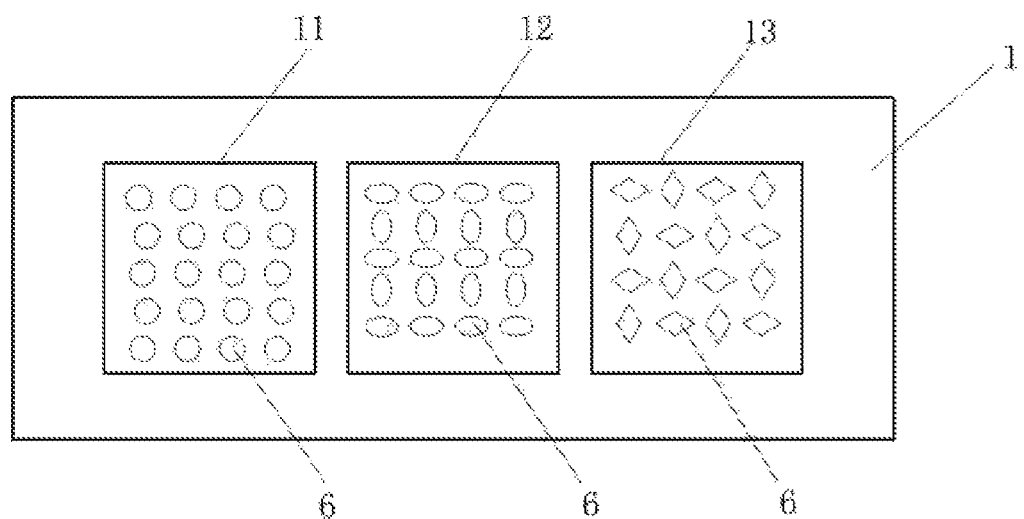
FIG. 11 is a structural diagram of the spectrometer according to Embodiment III of the present disclosure.

Specifically, as shown in FIG. 11, three modulation units 5, which are respectively a first modulation unit 11, a second modulation unit 12, and a third modulation unit 13, are distributed on a base plate of the optical modulation layer 1. In this embodiment, the modulation holes 6 inside the first modulation unit 11 are all circular, and each of the modulation holes 6 has the same structural parameters; the first modulation unit 11 has a first modulating mode with respect to the input spectrum. The modulation holes 6 inside the second modulation unit 12 are all oval, and each of the modulation holes 6 is arranged row by row in a periodic manner according to the sizes of the structural parameters, that is, the horizontally disposed oval modulation holes 6 and the vertically disposed oval modulation holes 6 are staggered row by row; the second modulation unit 12 has a second modulating mode with respect to the input spectrum. The modulation holes 6 inside the third modulation unit 13 are all rhombic, and each of the modulation holes 6 is arranged row by row and column by column in a periodic manner according to the sizes of the structural parameters, that is, the horizontally disposed rhombic modulation holes 6 and the vertically disposed rhombic modulation holes 6 are staggered row by row, and at the same time the horizontally disposed rhombic modulation holes 6 and the vertically disposed rhombic modulation holes 6 are staggered column by column; the third modulation unit 12 has a third modulating mode with respect to the input spectrum.

It can be understood that, the "a certain modulating mode for light having different wavelengths" in this embodiment may include, but is not limited to, effects such as scattering, absorption, transmission, reflection, interference, surface plasmon polariton, resonance and etc. The first, second and third light modulating methods are different from each other.

By the arrangements of the modulation holes 6 inside the modulation units 5, the differences in spectral responses between different units can be improved, and by increasing the number of the units, the sensitivity to the differences between different spectra can be improved.

It can be understood that, for measuring different incident spectra, the modulation role can be changed by adjusting the structural parameters of the modulation holes 6 inside each modulation unit 5. The adjustment of the structural parameters includes, but is not limited to one of the various parameters of the two-dimensional graphic structure, such as the arrangement period of the modulation holes, modulation hole radius, side length, duty ratio, and thickness of the modulation unit, and etc., or any combination thereof. In this embodiment, the duty ratio refers to a ratio of the area of the modulation holes 6 to the total area of the optical modulation layer 1.

It can be understood that, the micro-integrated spectrometer 300 of this embodiment may apply the modulation unit 5 of Embodiment I, or the modulation unit 5 of Embodiment II, or a combination of the modulation units 5 of Embodiment I and Embodiment II.

In this embodiment, the optical modulation layer 1 is made of a silicon nitride flat panel having a thickness of 200 nm to 500 nm. The optical modulation layer 1 is provided with 100 to 200 modulation units 5 in total, and each of the modulation units 5 has a length of 4 μm to 60 μm and a width of 4 μm to 60 μm. Various geometrical shapes are selected inside each of the modulation units 5 as the specific cross-sectional shapes of the modulation holes 6. Each of the modulation units 5 has a periodic arrangement of the same shape, and its duty ratio is 10% to 90%. The remaining structures are the same as those of Embodiment I or Embodiment II.

Figure 12:
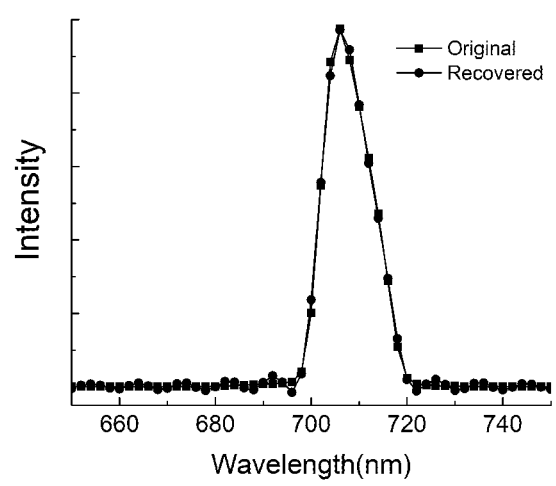
FIG. 12 is a diagram illustrating a wavelength-intensity relation of the spectral detection according to Embodiment III of the present disclosure.
Figure 13:
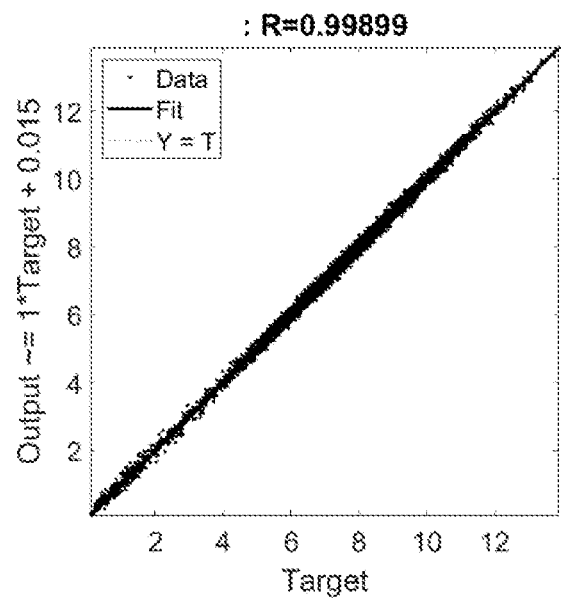
FIG. 13 is an effect diagram of the spectral detection according to Embodiment III of the present disclosure.

FIG. 12 and FIG. 13 each illustrates a spectral analysis effect during spectral analysis with the spectrometer 300 obtained through actual preparation according to the embodiments above. The optical modulation layer 1 described in this embodiment is mainly configured to detect the spectrum having a single-wavelength. The relation between the wavelength and the intensity is shown in FIG. 12. The central wavelength error between the measured spectrum and the actual spectrum is less than 0.4 nm. The detection effect is shown in FIG. 13. The accuracy of the light intensity is greater than 99.89%.

Embodiment IV

Figure 14:
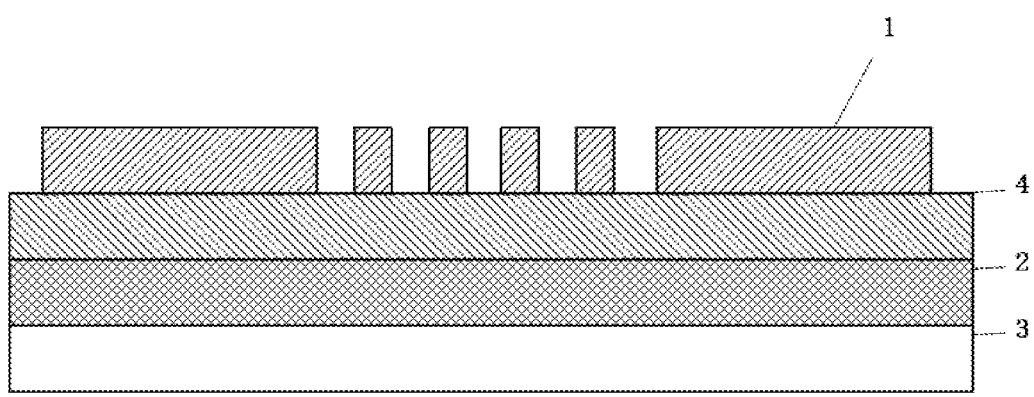
FIG. 14 is a sectional view of the spectrometer according to Embodiment IV of the present disclosure.

Based on the structures, principles, spectrum modulating methods and preparation methods of the spectrometer 300 of any of the embodiments above, Embodiment IV provides a spectrometer 300, and a spectrum modulating method. The same contents between this embodiment and the various embodiments above are not described repeatedly, while the differences are as follows:

as shown in FIG. 14, the spectrometer 300 in this embodiment further includes a light-transmitting medium layer 4 located between the optical modulation layer 1 and the photoelectric detection layer 2. Specifically, the light-transmitting medium layer 4 has a thickness of 50 nm to 1 μm, and the material may be silicon dioxide.

In the spectrometer 300 described in this embodiment, when a process scheme of directly growing by deposition is applied in the preparation of the optical modulation layer 1, the light-transmitting medium layer 4 may be covered on the photoelectric detection layer by chemical vapor deposition, sputtering, and spin coating, then the deposition and etching of the optical modulation layer 1 may be performed on the top of the light-transmitting medium layer 4. When a transfer process scheme is applied, silicon dioxide can be used as a preparation substrate for the optical modulation layer 1, and the optical modulation layer 1 is prepared by directly processing on an upper half of the substrate with micro-nano drilling, then a lower half of the silicon dioxide substrate is directly used as the light-transmitting medium layer 4, and the prepared optical modulation layer 1 and the light-transmitting medium layer 4 are transferred to the photoelectric detection layer as a whole.

It can be understood that, the light-transmitting medium layer 4 of this embodiment may also be arranged as that, the optical modulation layer 1 on the photoelectric detection layer 2 as a whole is supported through an external support structure, so that the optical modulation layer 1 is suspended with respect to the photoelectric detection layer 2. As a result, an air portion between the optical modulation layer 1 and the photoelectric detection layer 2 is the light-transmitting medium layer 4.

Embodiment V

On the basis of Embodiment II, Embodiment V further provides a spectrometer 300 and a spectrum modulating method. The same contents as those of Embodiment II are not described repeatedly in this embodiment, while the differences are as follows:

the optical modulation layer 1 of this embodiment is made based on a horizontally disposed silicon carbide base plate having a thickness of 150 nm to 300 nm. There are 150 to 300 units on the optical modulation layer 1, and each of the units has a length of 15 to 20 μm and a width of 15 to 20 μm. Each of the modulation holes 6 inside a same modulation unit 5 has a circular specific cross-sectional shape, and the parameters of each of the modulation units 5 such as the circular hole arrangement period, the hole radius, the duty ratio and etc. are different from each other. The specific parameter range is: the period range is 180 nm to 850 nm, the hole radius range is 20 nm to 780 nm, and the duty ratio range is 10% to 92%. The photoelectric detection layer 2 is equipped with at least one InGaAs detector.

The preparation process of the spectrometer 300 of this embodiment is a transfer process in which the optical modulation layer 1 is firstly prepared and then transferred to the photoelectric detection layer 2.

Embodiment VI

Figure 15:
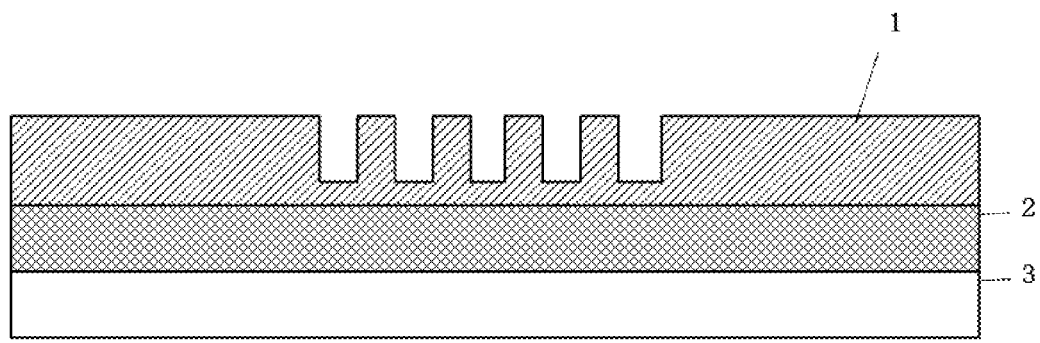
FIG. 15 is a sectional view of the spectrometer according to Embodiment VI of the present disclosure.

Based on the structures, principles, spectrum modulating methods and preparation methods of the spectrometer 300 of any of the embodiments above, Embodiment VI provides a spectrometer 300 and a spectrum modulating method. The same contents between this embodiment and the various embodiments above are not described repeatedly, while the differences are as follows:

as shown in FIG. 15, in the spectrometer 300 of this embodiment, respective modulation holes 6 do not penetrate the base plate. It can be understood that, whether the modulation hole 6 penetrates the base plate or not will have no adverse effect on the modulation role of the optical modulation layer 1. This is because that the silicon-based material or other materials selected for the optical modulation layer 1 are light-transmitting materials. When a spectrum is incident into the optical modulation layer 1, a modulation role occurs due to effect of the structure of each of the modulation units 5, but the bottom of the modulation holes 6 has no adverse effect on the spectrum modulation.

In the spectrometer 300 of this embodiment, the thickness from the bottom of the modulation holes 6 of the optical modulation layer 1 to the bottom of the base plate is 60 nm to 1200 nm, and the entire base plate has a thickness of 120 nm to 2000 nm.

Embodiment VII

Figure 16:
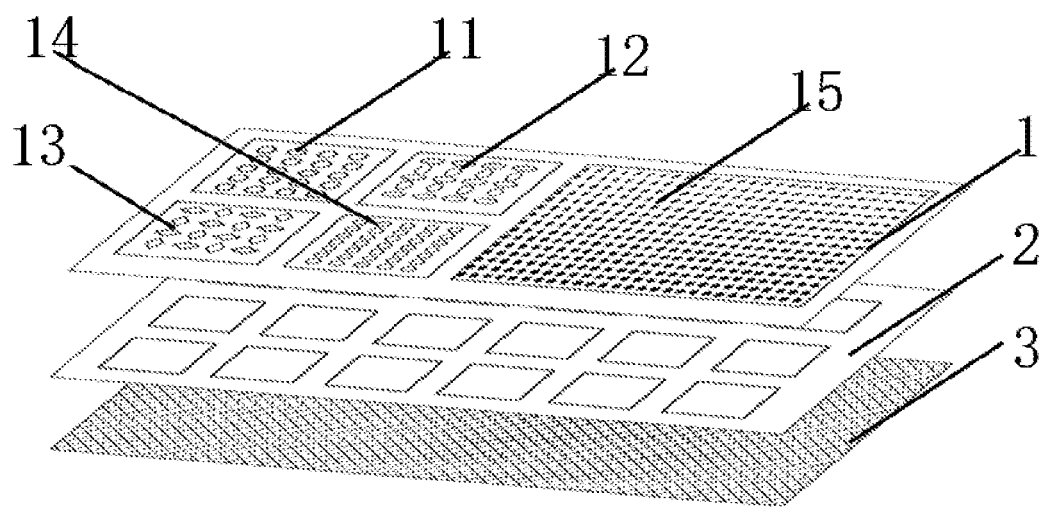
FIG. 16 is a sectional view of the spectrometer according to Embodiment VII of the present disclosure.
Figure 17:
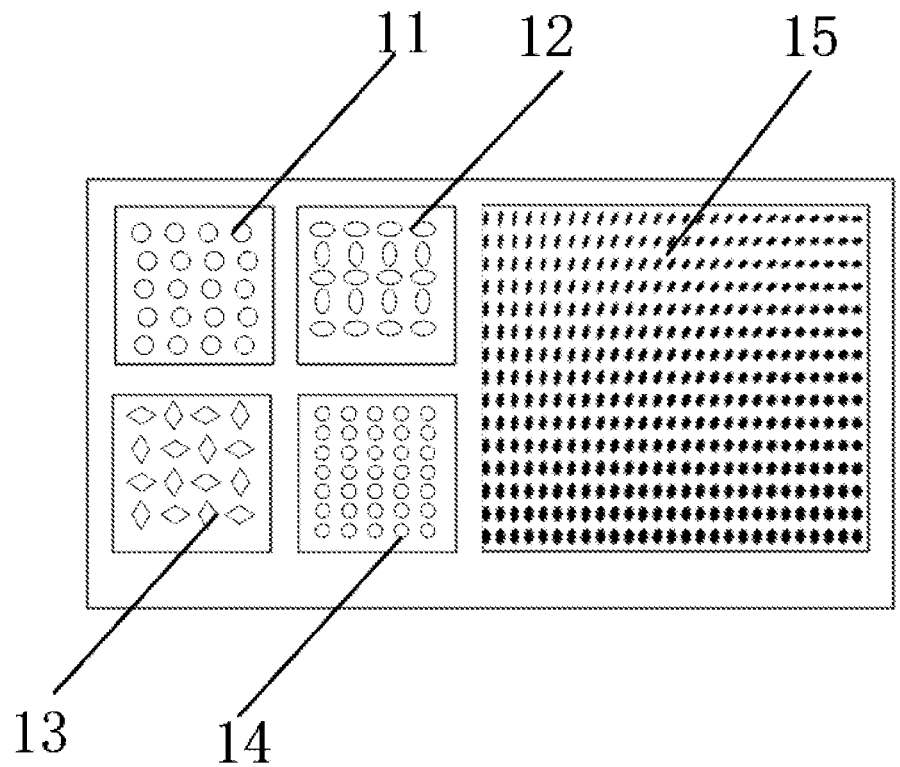
FIG. 17 is a diagram of the spectrometer according to Embodiment VII of the present disclosure.

Based on the combinations of the various embodiments above, Embodiment VII provides a spectrometer 300 and a spectrum modulating method. The same contents between this embodiment and the various embodiments above are not described repeatedly, while the differences are as follows:

as shown in FIG. 16 and FIG. 17, in the spectrometer 300 of this embodiment, five modulation units 5, which are a first modulation unit 11, a second modulation unit 12, a third modulation unit 13, a fourth modulation unit 16 and a fifth modulation unit 17, respectively, are distributed on the base plate of the optical modulation layer 1. In this embodiment, the fifth modulation unit 15 has the largest range, and its area is not smaller than the total area of the former four modulation units.

Specifically, the first modulation unit 11, the second modulation unit 12, the third modulation unit 13, and the fourth modulation unit 14 are arranged in a matrix as a whole, wherein, the modulation holes 6 inside the first three modulation units 11, 12 and 13 are arranged in a same manner as that of the modulation holes 6 of Embodiment III. The modulation holes 6 of the fourth modulation unit 14 and the first modulation unit 11 have the same and circular specific cross-sectional shapes, but the modulation holes 6 of the fourth modulation unit 14 have different structural parameters from those of the modulation holes 6 of the first modulation unit 11. Specifically, the inner diameters of the modulation holes 6 of the fourth modulation unit 14 are smaller than those of the modulation holes 6 of the first modulation unit 11. Therefore, the fourth modulation unit 14 has a fourth modulating mode for the input spectrum. The two-dimensional graphic structure formed by each of the modulation holes 6 inside the fifth modulation unit 15 is the same as that of Embodiment I, and the fifth modulation unit 15 has a fifth modulating mode for the input spectrum.

It can be seen from above that, the optical modulation layer 1 of this embodiment VII uses the differences in the specific cross-sectional shapes of different modulation holes 6 between different units, and the specific arrangement of the modulation holes 6 in a same unit, to implement different modulation roles on the spectrum with different wavelengths by adjusting the specific cross-sectional shapes of the modulation holes 6, the structural parameters of the modulation holes 6 and the arrangement period of the modulation holes 6.

It can be understood that, for the structures of the gradual array modulation units 5 that are arranged according to Embodiment I and Embodiment II, the modulation units 5 arbitrarily divided have different modulating roles on the spectrum. In theory, an infinite number of modulated spectrum samples can be obtained, which dramatically increases the amount of data for reconstructing the original spectrum, and is helpful for restoring the spectral pattern of the broadband spectrum.

As for the structure of the periodic modulation units 5 according to Embodiment III, it can generate the dispersion and resonance effects of the two-dimensional period. The resonance role includes, but is not limited to, the principles of energy band control of photonic crystal, resonance of the two-dimensional grating and etc. The detection accuracy for specific wavelengths can be enhanced through resonance.

When the modulation units 5 in Embodiment I, Embodiment II and Embodiment III are applied to a chip at the same time, the two advantages above can be integrated. When the size range of the optical modulation layer is cut, the spectrometers 300 of the three embodiments above can be prepared into structures of the order of micrometers or even smaller, which is of great significance for the miniaturization and micromation manufacture and use of the spectrometers 300. The above-mentioned optical modulation layer 1 is cooperated with a photoelectric detector composed of different photoelectric detectors, which, in principle, can achieve the full-wave band spectral detection, thereby making the broad-spectrum detection performance of the spectrometer 300 better.

In summary, the noninvasive glucometer of this embodiment includes a light source 100, a spectrometer 300 and detecting space into which the object to be detected intervenes. The detecting space is connected with the light source and the spectrometer 300 respectively, so that the spectrum emitted by the light source can generate incident light that enters the spectrometer 300 after passing through the object to be detected. The incident light has been affected by the object to be detected because it passes through the object to be detected. Therefore, spectral analysis and reconstruction are performed on the incident light by the spectrometer 300 to obtain the spectral data containing blood glucose parameters, so that the non-contact and non-invasive blood glucose detecting of the biological object to be detected is achieved using the principle of near-infrared spectral analysis.

The spectrometer 300 in the noninvasive glucometer 300 includes: an optical modulation layer configured to perform light modulation on the incident light to obtain a modulated spectrum; a photoelectric detection layer located below the optical modulation layer, and configured to receive the modulated spectrum and provide differential responses with respect to the modulated spectrum; and a signal processing circuit layer located below the photoelectric detection layer and configured to reconstruct the differential response to obtain an original spectrum. The spectrometer 300 of the noninvasive glucometer replaces various types of precise optical components in the existing spectrometers with the optical modulation layer, so as to achieve the application of the spectrometer 300 in the field of micro-nano structures, so that the micro-integrated spectrometer 300 can operate without gratings, prisms, reflecting mirrors or other similar spatial beam splitting elements, and thus the size of the spectrometer 300 is significantly reduced meanwhile the precision of spectral analysis is improved. Therefore, the noninvasive glucometer has the advantages of high measurement accuracy, good portability, real-time online detection, simple operation, stable performance, low manufacturing costs and etc., which can greatly improve the life quality of the patients suffered from diabetes mellitus and has a broad market prospect.

The embodiments of the present disclosure are presented for the purposes of illustration and description, and are not exhaustive or to limit the present disclosure to the disclosed forms. Many modifications and variations are obvious to the person of ordinary skills in the art. The embodiments are selected and described in order to better illustrate the principles and practical applications of the present disclosure, and to make the person of ordinary skills in the art to appreciate the present disclosure so as to design various embodiments suitable for specific uses and having various modifications.

In the description of the present disclosure, unless specified otherwise, both "a plurality of" and "several" mean two or more; unless specified otherwise, "notch" means the shapes other than the shape with a flush cross section. The orientation or position relations indicated by the terms "upper", "lower", "left", "right", "inner", "outer", "front end", "rear end", "head portion", "tail portion" etc. are based on the orientation or position relations shown in the drawings, which is merely for the convenience of describing the present disclosure and simplifying the description, and is not to indicate or imply that the device or component referred to must have a specific orientation, be constructed and operated in the specific orientation. Therefore, it cannot be construed as limiting the present disclosure. In addition, the terms "first", "second" and "third" etc. are for the purpose of description, and cannot be construed as indicating or implying the relative importance.

In the description of the present disclosure, it should be noted that unless specifically defined or limited, the terms "mount", "connect with", and "connect to" should be understood in a broad sense, for example, they may be fixed connections or may be removable connections, or integrated connections; may be mechanical connections or electrical connections; may be direct connections or indirect connections through intermediate mediums. For a person of ordinary skills in the art, the specific meanings of the terms above in the present disclosure can be understood according to specific situations.

The invention claimed is:

1. A noninvasive glucometer, comprising a light source and a spectrometer; wherein, a spectrum emitted by the light source generates incident light entering the spectrometer after passing through an object to be detected;

the spectrometer comprises:
an optical modulation layer, the optical modulation layer comprising a base plate and one or more modulation units, the one or more modulation units being located on the base plate, each of the one or more modulation units being provided with several modulation holes, each of the modulation holes being configured to perform light modulation on the incident light to obtain a modulated spectrum, and the modulated spectrum being a broadband spectrum;
a photoelectric detection layer located below the optical modulation layer, and configured to receive the modulated spectrum and provide a differential response with respect to the modulated spectrum; and
a signal processing circuit layer located below the photoelectric detection layer and configured to reconstruct an original spectrum utilizing the differential response,
wherein the optical modulation layer is made of silicon, germanium, silicon germanium materials, silicon compounds, germanium compounds, or III-V group materials.

2. The noninvasive glucometer of claim 1, wherein the base plate is provided on the photoelectric detection layer, and the respective modulation holes in each of the modulation units are arranged into a two-dimensional graphic structure.

3. The noninvasive glucometer of claim 2, wherein, the two-dimensional graphic structure comprises that:
all the modulation holes inside respective two-dimensional graphic structures have the same specific cross-sectional shapes and the respective modulation holes are arranged in an array in an order that sizes of structural parameters are gradually varied; and/or the respective modulation holes inside the respective two-dimensional graphic structures respectively have a specific cross-sectional shape, and the respective modulation holes are combined and arranged according to the specific cross-sectional shape.

4. The noninvasive glucometer of claim 3, wherein, an arrangement order is being arranged row by row or column by column according to a preset period order when the respective modulation holes are arranged and combined according to the specific cross-sectional shape.

5. The noninvasive glucometer of claim 2, wherein a bottom of at least one of the modulation holes penetrates the base plate.

6. The noninvasive glucometer of claim 1, wherein the photoelectric detection layer comprises one or more detection units, the one or more detection units are correspondingly provided below each modulation unit of the optical modulation layer, and the one or more detection units are electrically connected through the signal processing circuit layer.

7. The noninvasive glucometer of claim 1, wherein, the spectrometer further comprises:
a light-transmitting medium layer located between the optical modulation layer and the photoelectric detection layer.

8. The noninvasive glucometer of claim 1, wherein the light source and the spectrometer are respectively provided on both sides of the object to be detected; or
the light source and the spectrometer are arranged on one side of the object to be detected.

9. The noninvasive glucometer of claim 1, further comprising:
a data processing module connected to the signal processing circuit layer and configured to perform analysis and calculation on the original spectrum to obtain blood glucose parameters; and
a data display module connected to the data processing module and configured to display the blood glucose parameters.

10. A blood glucose detection method based on the glucometer of claim 1, comprising:
moving the object to be detected into a detecting space connected with the light source and the spectrometer, so that the spectrum emitted by the light source passes through the object to be detected and the incident light entering the spectrometer is generated;
performing the light modulation on the incident light through the modulation holes to obtain the modulated spectrum, wherein the modulated spectrum is a broadband spectrum;
receiving the modulated spectrum and providing the differential response with respect to the modulated spectrum; and
reconstructing the original spectrum utilizing the differential response.

11. The noninvasive glucometer of claim 2, wherein, the spectrometer further comprises:
a light-transmitting medium layer located between the optical modulation layer and the photoelectric detection layer.

12. The noninvasive glucometer of claim 3, wherein, the spectrometer further comprises:
a light-transmitting medium layer located between the optical modulation layer and the photoelectric detection layer.

13. The noninvasive glucometer of claim 4, wherein, the spectrometer further comprises:
a light-transmitting medium layer located between the optical modulation layer and the photoelectric detection layer.

14. The noninvasive glucometer of claim 5, wherein, the spectrometer further comprises:
a light-transmitting medium layer located between the optical modulation layer and the photoelectric detection layer.

15. The noninvasive glucometer of claim 6, wherein, the spectrometer further comprises:
a light-transmitting medium layer located between the optical modulation layer and the photoelectric detection layer.

16. The noninvasive glucometer of claim 2, wherein the light source and the spectrometer are respectively provided on both sides of the object to be detected; or
the light source and the spectrometer are arranged on one side of the object to be detected.

17. The noninvasive glucometer of claim 3, wherein the light source and the spectrometer are respectively provided on both sides of the object to be detected; or
the light source and the spectrometer are arranged on one side of the object to be detected.

18. The noninvasive glucometer of claim 4, wherein the light source and the spectrometer are respectively provided on both sides of the object to be detected; or
the light source and the spectrometer are arranged on one side of the object to be detected.

* * * * *